United States Patent [19]

Strobel

[11] Patent Number: 4,588,693
[45] Date of Patent: May 13, 1986

[54] DEVELOPMENT OF PLANT ROOTS

[75] Inventor: Gary A. Strobel, Bozeman, Mont.

[73] Assignee: Research and Development Institute, Inc. at Montana State University, Bozeman, Mont.

[21] Appl. No.: 470,392

[22] Filed: Feb. 28, 1983

[51] Int. Cl.$^4$ .................. C12N 1/20; C12N 15/00; A01B 79/00; A01C 1/00
[52] U.S. Cl. .................. 435/253; 435/172.3; 47/1 R; 47/58
[58] Field of Search .................. 435/172, 253, 172.3; 47/1 R, 58

[56] References Cited

U.S. PATENT DOCUMENTS 4,425,150  1/1984  Strobel et al. .................. 71/77

OTHER PUBLICATIONS

Chilton et al., Nature, vol. 295, pp. 432–434, Feb. 4, 1982.
Roberts et al., Nature, vol. 265, pp. 379–381.
White et al., Journal of Bacteriology, vol. 144, pp. 710–720, Nov. 1980.
Hilderbrand, Journal of Agricultural Research, vol. 48, pp. 857–885 (1934).
Moore et al., Plasmid vol. 2, pp. 617–626, 1979.
Moore, Plant Disease, p. 439, May 1982.
Moller et al., Biological Control of Crown Gall, Aug. 1976.
"Genetic Information on the Ri Plasmid of *Agrobacterium rhizogenes* Determines Host Specificity" by Lam et al., *Plant Science Letters*, 34 (1984), pp. 345–353.
"Hairy Root: Plasmid Encodes Virulence Traits in *Agrobacterium rhizogenes*", by White and Nester, Journal of Bacteriology, vol. 141, No. 3, Mar. 1980, pp. 1134–1141.
American Type Culture Collection documentation dated Nov. 5, 1982 regarding Budapest Treaty on the Int'l. Recognition of the Deposit of Microorganisms for the Purposes of Patent Procedure (2 p.).
"GALLTROL TM for Preventive Bio-Control of Crown Gall", brochure by AgBioChem, Inc. of Orinda, California (undated).
"The Position of *Agrobacterium rhizogenes*" by J. M. Jaynes and G. A. Strobel, *International Review of Cytology* (Supplement 13), 1981, pp. 105–125.

Primary Examiner—Alvin E. Tanenholtz
Attorney, Agent, or Firm—Christie, Parker & Hale

[57] ABSTRACT

Beneficial growth of roots in dicotyledonous plants is achieved by genetic transformation with root-inducing *A. rhizogenes*, preferably the novel strain *A. rhizogenes* ATCC 39207. The *A. rhizogenes* not used to transform the plant is reduced to noninfective levels with *A. radiobacter*, preferably *A. radiobacter* K-84.

39 Claims, 3 Drawing Figures

DEVELOPMENT OF PLANT ROOTS

BACKGROUND OF THE INVENTION

*Agrobacterium rhizogenes* is the causal organism of what has been termed "the hairy root disease" in a number of species of higher plants. *A. rhizogenes* can be isolated from the soil, and is a species of agrobacterium which has the following characteristics: aerobic, rod-shaped (0.8×1.50–30 micron), one to four peritrichous flagella, Gram negative, and nonspore forming. The common species are *A. tumefaciens,* which is tumor-causing; *A. rhizogenes,* which causes hairy-root disease; and *A. radiobacter,* which is nonpathogenic.

The potential of using *A. rhizogenes* to the benefit of man was mentioned in an article entitled, "Studies on Infectious Hairy Root of Nursery Apple Trees," *Journal of Agricultural Research,* Vol. 41, No. 7, pp. 507–540, A. J. Riker et al. The authors state at 537, "In preliminary experiments cuttings or layers of certain plants treated with the hairy-root organism have rooted sooner and more vigorously than those untreated. These results suggest the possibility of using this organism to stimulate root production in the propagation of certain plants. More work is necessary before conclusions can be drawn." Despite this invitation, *A. rhizogenes* has not been actively pursued to the benefit of man, and remains regarded as an undesired pathogen.

SUMMARY OF THE INVENTION

It has now been found that one can effectually cause the controlled beneficial growth of roots in dicotyledonous plants by genetic transformation with root-inducing *A. rhizogenes,* preferably a novel strain designated as *Agrobacterium rhizogenes* ATCC 39207. The control exists in that functional *A. rhizogenes* has or exhibits an undesired potential to contaminate soil, either can be effectively controlled by the use of *Agrobacterium radiobacter,* preferably *A. radiobacter* K-84, used in conjunction with or following genetic transformation of the plant with *A. rhizogenes.* Independent of which *A. rhizogenes* is used, a plant is transformed by contact of the exposed pericycle of the plant with *A. rhizogenes* in an aqueous suspension or other medium, such as peat, preferably at an effective concentration of at least about $10^8$ cells per ml, for a period of time to achieve transformation. Uniform results are obtained by an exposure of at least about 20 hours. The presently preferred exposure for the stated concentration is at least about 24 hours. Irreversible transformation occurs. Any *A. rhizogenes* then remaining on the surface of the plant is superfluous to root development. It can therefore be reduced to noninfective levels by exposure to *A. radiobacter.* A simple dip is all that is required in an aqueous suspension in which the *A. radiobacter* concentration is from about $10^7$ to about $10^9$ cells/ml. Conveniently, it has been found that transformation may be accomplished by combining *A. rhizogenes* with *A. radiobacter* in the same treating solutions, in a cell ratio of at least about 4 to 1, preferably from about 4 to 1 to about 8 to 1 *A. rhizogenes* to *A. radiobacter.* Presently preferred solutions contain about $10^9$ cells of *A. rhizogenes* and about $2.5 \times 10^8$ cells of *A. radiobacter* per ml. Contact, again, is for at least about 20 hours. With such treatment, essentially no viable *A. rhizogenes* remains on the exposed surface of the transformed plant to create a problem of soil contamination.

In either event, both *A. rhizogenes* and *A. radiobacter,* alone or in combination, will withstand pelletizing by centrifugation and lyophilization to yield dry, viable cells. In addition, they may be, and preferably are, supported by other media such as neutral to alkaline peat to be used directly by application to the receptive zone of the plant for the prescriptive period of time or from which the organism(s) are extracted for use in aqueous solution.

*A. rhizogenes* ATCC 39207 has been established to be more effective than its source for root development exhibiting the potential of doubling root growth in the same amount of time.

THE DRAWINGS

Figure 3:
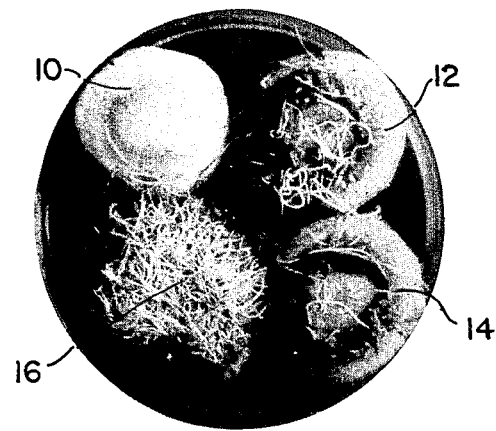

FIG. 3 illustrates carrot disks cut from the same carrot. With reference thereto, disk 10 is a control as was not transformed. Disks 12 and 14 were transformed with *A. rhizogenes* TR 105. Disk 16 was transformed with *A. rhizogenes* ATCC 39207.

DETAILED DESCRIPTION

According to the present invention, there is provided a novel strain of *A. rhizogenes,* namely, *A. rhizogenes* ATCC 39207, which was isolated from *A. rhizogenes* TR 105, which may be used alone or in combination with other root-inducing *A. rhizogenes* for genetic transformation of dicotyledonous plants to enhance root development, with control of the *A. rhizogenes* being available through the use of *A. radiobacter,* preferably *A. radiobacter* K-84.

A plant genetically transformed with *A. rhizogenes* may be subsequently treated with *A. radiobacter* or the two combined, to achieve transformation without leaving an infective residue of *A. rhizogenes* on the surface of the plant. If the two are combined, they may be combined in a cell ratio of about 4 to 1 or more *A. rhizogenes* to *A. radiobacter,* preferably from about 4 to 1 to about 8 to 1, with *A. radiobacter* serving to substantially prevent the *A. rhizogenes* contaminating the soil without interfering with plant transformation. Transformation of a plant with *A. rhizogenes* in all cases requires exposure to the pericycle, since the organism is noninvasionary. Exposure is for a time sufficient for genetic transformation to occur. It is presently preferred that effective exposure to transforming *A. rhizogenes* be for at least about 20 hours, preferably at least about 24 hours. Transformation generally requires exposure of *A. rhizogenes* to a wound of the plant, either created by means of a cut (whether or not new) or simply through severed roots. *A. rhizogenes* concentration in a treating medium is normally at least about $10^8$ cells/ml, preferably at least about $10^9$ cells/ml. Lower concentrations are also useful but may require longer exposure for transformation to occur. It may be provided as an aqueous solution or through a carrier, such as peat, which is brought into contact with the receptive, exposed surface of the plant, and from which transformation occurs by cell diffusion. In the alternative, the contained organism(s) may be extracted from the peat into an aqueous solution used for transformation of the plant.

Benefits of the use of *A. rhizogenes* in accordance with the instant invention are many. It may be employed, first of all, to promote early rooting of bare-root stock, leading to more leaf development, both in size and number; less die-back of limbs and stems; an increase in opportunity for fruit development during first-season planting; reduced pruning of the tree prior to planting; and, significantly, increasing the potential of the plant to survive drought. The same benefits may be induced to plant cuttings, where cut stems are placed in mist benches until sufficient roots develop. In this instance, more root development per unit of time can be expected by practice of the instant invention. The invention may also be employed in transplanting of larger plants, such as trees, which are well known to undergo shock during the process of transplanting. Transformation with *A. rhizogenes* through cut roots can be used to promote rapid development of new roots at locale of root cleavage, allowing adequate moisture take-up by the tree to prevent leaf-drop and tree death.

Finally, plants suffering from root damage or disease may also be benefited by treatment with *A. rhizogenes* to promote the rapid development of new root growth to counteract those undergoing degeneration.

Despite the potential benefits of the invention, *A. rhizogenes* may remain regarded as a soil pathogen. In this instance, its effect can be eliminated or diminished to noninfective levels through the use of *A. radiobacter*. *A. radiobacter* K-84 is presently preferred. *A. radiobacter* K-84 is cultured and sold by AgBioChem, Inc., 3 Fleetwood Court, Orinda, Calif. 94563. One can simply dip the transformed plant into an aqueous solution of *A. radiobacter*, preferably present in a concentration in excess of about $10^7$ cells/ml, for but seconds to effectively terminate the active *A. rhizogenes*.

More conveniently, the two may be combined in a common transforming medium. When present in a cell ratio of *A. rhizogenes* to *A. radiobacter* of at least about 4 to 1, preferably from about 4 to 1 to about 8 to 1, transformation can occur without leaving a residue of active *A. rhizogenes* on the plant. In this instance, as in the instance of the use of *A. rhizogenes* alone, transformation requires exposure of a receptive plant area to the transforming organism. However, the *A. radiobacter* does not appear to interfere with the transformation process.

Peat has been found to be an excellent host for the organisms. Organisms have been found to thrive in essentially neutral to alkaline (pH) peat, which serves as a convenient carrier and an effective treating medium. Lyophylization can also be employed. If peat is employed, the *A. rhizogenes* is kept separate from the *A. radiobacter* and the peat units carrying them are combined at the time of use.

Without limitation, the following illustrate the invention. In connection with plantings in ground, plantings, unless otherwise indicated, were made during the normal planting season for the 45th parallel for the State of Montana, United States of America.

Examples 1 to 4 and Controls A to D

Bare-root plum trees averaging from 4 to 5 feet in height, were root-wounded, then treated with *A. rhizogenes* TR 105, provided by Dr. Nester, Department of Microbiology and Immunology, University of Washington, Seattle, Wash. 98195, by submersing the wounded area of the plant into a solution containing *A. rhizogenes* at a cell-suspension concentration of about $9 \times 10^9$ cells per millimeter for 24 hours. The control roots were submerged in water alone. Treated and control stocks were stored at 40° F. until time for planting, and were then planted in a soil/vermiculite 1:1 mix in the field. The trees were watered every three days for nine days, then natural rainfall was relied upon for root development. After a period of about 30 days, the plants were gently removed from the soil and rinsed with water. The new roots were picked, with the aid of tweezers, from the old roots, then dried and weighed. The results are shown in Table I.

TABLE I

| NEW ROOT WEIGHT | | | |
|---|---|---|---|
| Example | Transformed Plant (g) | Control | (g) |
| 1 | .025 | A | .004 |
| 2 | .018 | B | .009 |
| 3 | .019 | C | .014 |
| 4 | .012 | D | .006 |
| x̄ | .019 | x̄ | .008 |

Significant difference is at the level

Significant difference is at the 0.1 level

Examples 5 to 8 and Controls E to H

Other plum trees from the same source as those used for Examples 1 to 4 and Controls A to D were treated in the same manner, but measured for leaf development. The measurements were respectively taken at the end of midsummer and about two weeks later. The results are shown in Table II.

TABLE II

| LEAF DEVELOPMENT | | | | | |
|---|---|---|---|---|---|
| Example | Transformed Plant Leaf Size (cm) | No. of Leaves | Control | Leaf Size (cm) | No. of Leaves |
| 5 | 3.919 length 2.725 width | 155 | E | 2.028 length 1.740 width | 53 |
| 6 | 4.183 length 2.253 width | 170 | F | 1.920 length 1.680 width | 104 |
| 7 | 5.124 length 4.001 width | 113 | G | 2.529 length 2.109 width | 115 |
| 8 | 4.501 length 4.173 width | 158 | H | 2.348 length 2.440 width | 147 |
| Total | | 596 | | | 419 |

All differences between treatments and controls are significant at the 0.01 level.

Examples 6 to 11 and Controls I to K

Figure 1:
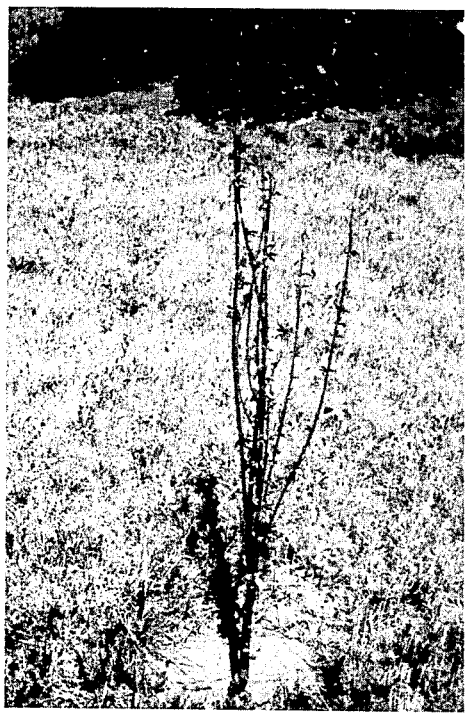
FIG. 1 is a photo of a control North Star cherry tree taken 45 days after planting, illustrating the degree of leaf development.
Figure 2:
FIG. 2 is a photo of a transformed North Star cherry tree taken 45 days after planting, illustrating the increased leaf development.

North Star cherry trees averaging about 4 feet tall taken from bare-root stock were root-wounded for both the treatment and controls. Following the procedure of Examples 1 to 4, injured roots were transformed with a solution containing about $1.6 \times 10^{10}$ cells of *A. rhizogenes* TR 105 per milliliter, soaked overnight, and left in dark, cold storage for 18 days. Planting occurred early in the planting season. The transformed plants blossomed five days after budding. It took the controls an additional 10 days to blossom. Approximately 45 to 50 days after planting, cherries were observed on the transformed plants, and a leaf, stem and cherry count was made in midsummer. With significant difference at the 0.05 level, the comparison of transformed to control, the number of leaves, number of cherries, number of branches, die-back and leaf length were observed, as reported in Table III. FIG. 1 is a photo of control plant about 45 days after planting. FIG. 2 is a photo of a transformed plant which has been exposed to the same growth conditions as those of the plant shown in FIG. 1, except for the use of *A. rhizogenes* to promote root growth. In addition to the apparent differences, there was also more root spur formation, which is indicative of higher flower and root development in the following years of growth.

TABLE III

|  | No. of Leaves | No. of Ripened Cherries | No. of Branches Died Back | Leaf Length (cm) |
|---|---|---|---|---|
| Example #9 | 590 | 3 | 6/13 | 6.5 |
| Example #10 | 707 | 9 | 5/14 | 6 |
| Example #11 | 593 | 0 | 1/07 | 6 |
| Control I | 0 | 0 | 15/15 | — |
| Control J | 351 | 0 | 10/16 | 4.2 |
| Control K | 374 | 0 | 6/10 | 2.5 |

Example 12 and Control L

*A. rhizogenes* ATCC 39207 was derived from *Agrobacterium rhizogenes* TR 105 by screening isolated single colonies of TR 105 on carrot root disks until a change was observed in the degree of root development. A treating solution was made of *Agrobacterium rhizogenes* TR 105 to a to a cell concentration of $2.1 \times 10^9$ cells per milliliter, and a comparison solution of *A. rhizogenes* ATCC 39207 at a cell concentration of $4 \times 10^9$ cells per milliliter. Carrot disks were treated at a concentration of 0.1 milliliter per carrot disk and incubated for three weeks at room temperature. The results of the degree of root formation are shown in Table IV and illustrated in FIG. 3, explained at page 4 herein.

TABLE IV

|  | Carrot #1 | Carrot #2 | Carrot #3 | Carrot #4 |
|---|---|---|---|---|
|  | *A. rhizogenes* TR 105 | | | |
|  | .0025 | .0054 | .0000 | .0006 |
|  | .0010 | .0015 | .0060 | .0003 |
|  | .0011 | .0009 | .0037 | .0016 |
|  | .0030 | .0027 | .0020 | .0016 |
|  | .0043 | .0015 | .0003 | .0009 |
|  | .0076 | .0027 | .0017 | .0009 |
|  | .0030 | .0001 | .0034 | .0001 |
|  | .0053 | .0044 | .0042 | .0012 |
|  | .0030 | .0046 | .0013 | .0016 |
|  | .0096 | .0021 | .0047 | .0005 |
| $\bar{x}$ | .0040 | .0026 | .0027 | .0009 |
|  | *A. rhizogenes* ATCC 39207 | | | |
|  | .0024 | .0000 | .0001 | .0000 |
|  | .0101 | .0003 | .0015 | .0013 |
|  | .0036 | .0010 | .0022 | .0003 |
|  | .0113 | .0012 | .0007 | .0006 |
|  | .0118 | .0063 | .0012 | .0005 |
|  | .0093 | .0018 | .0035 | .0027 |
|  | .0078 | .0004 | .0058 | .0002 |
|  | .0123 | .0034 | .0019 | .0031 |
|  | .0127 | .0035 | .0011 | .0010 |
|  | .0006 | .0059 | .0051 | .0002 |
| $\bar{x}$ | .0082 | .0024 | .0023 | .0010 |

Data $\bar{x}$ for Carrot #1 are different TR 105 from ATCC 39207 at 0.05 level.

In the above work, cell density was about 130 cells per square inch of carrot-disk surface.

If a plant has the potential of being an excellent rooter, *A. rhizogenes* ATCC 39207 will at least double the dry weight of roots; otherwise, no difference is shown. *A. rhizogenes* ATCC 39207 is on viable deposit at the America Type Culture Collection, 12301 Parklawn Dr., Rockville, Md. 20852, and was initially given the identification *Agrobacterium rhizogenes* MT 232 by me.

Example 13 and Control M

Avocado-stem cuttings 10–12 cm in length were used for the control (80 test plants) and for transformation (100 test plants). To transform the plants, the cuttings were dipped in a suspension containing *A. rhizogenes* TR 105 at a concentration of $10^9$ cells/ml for 15 minutes. This insured inoculation with sufficient cells to achieve transformation. The cuttings were planted in a rooting mixture of 40% by weight perlite and 60% by weight peat. The cuttings were placed on a cloud 9 fogging system mist bench, and every 10 minutes the mist was applied during daylight hours only (16-hour days). Two months after planting, it was determined that 5 of the 80 control plants were alive and had produced leaves and roots, while 61 of the 100 transformed plants were alive and had produced leaves and roots.

Example 14 and Control L

The following is to establish that *A. rhizogenes* is effective in promoting root development in plants that are vegetatively propagated. Cuttings of stems with leaves of violets were dipped into a suspension of *A. rhizogenes* at a concentration of about $10^9$ cells per milliliter, and placed on the mist bench until rooting occurred. In this instance, the control plants gave an average of 0.002 grams dry weight of root development per plant, whereas transformed cuttings gave an average of 0.005 gram of roots per plant on a dry-weight basis. This is a significant difference at the 0.1 level. The observations were made two weeks after placement on the mist bench and shown in Table V.

TABLE V

| DRY WEIGHT OF ROOTS PRODUCED ON VIOLET-STEM CUTTINGS | |
|---|---|
| Control M | Example 14 |
| .0015 | .0043 |
| .0042 | .0038 |
| .0011 | .0040 |
| .0054 | .0063 |
| .0002 | .0030 |
| .0020 | .0028 |
| .0010 | .0036 |
| .0022 | .0034 |
| .0014 | .0103 |
| .0012 | .0026 |
| .0012 | .0054 |
| .0004 | .0064 |
| .0025 | .0056 |
| .0023 | .0086 |
| .0028 | .0050 |
| $\bar{x} =$ .0020 | $\bar{x} =$ .0050 |

Example 15 and Control M

Mango cuttings of approximately 10 cm. in length were transformed by dipping the lower 7 cm. into a bacterial suspension containing $7 \times 10^5$ cells of *A. rhizogenes* per milliliter. Forty mango cuttings were used for each test. The transformed cuttings and controls were placed on the mist bench and maintained at 70°–80° F. In the case of the controls, 41.0±7.5% of the cutting developed plants, whereas the *A. rhizogenes*-treated cuttings had 79%±7% develop into plants.

Example 16

To establish that *A. rhizogenes* ATCC 39207 does not contaminate the rhizoplasm or nearby soil, *Agrobacterium radiobacter* K-84 was used as a co-inoculant to treat the plant following treatment with *A. rhizogenes* separately or in conjunction therewith. Treatments following the contact with *A. rhizogenes* was only by a dip in the suspension of *A. radiobacter*. When used in combination, the cell ratio of *A. rhizogenes* to *A. radiobacter* was approximately 4 to 1, *A. rhizogenes* being present in a concentration of about $10^9$ cells per milliliter, and the *A. radiobacter* in a concentration of $2.5 \times 10^8$ cells per milliliter. In all instances, transformation with *A. rhizogenes* occurred during 24 hours. After rooting three to four weeks, carrot disks were rinsed with 0.1 milliliter of water, the rinse did not yield any infectious colonies of *A. rhizogenes* when placed onto another carrot disk.

What is claimed is:

1. Biologically pure *Agrobacterium rhizogenes* ATCC 39207.

2. A composition for the genetic transformation of dicotyledonous plants for the beneficial growth of roots which comprises:
   (a) root-inducing *A. rhizogenes* provided in a concentration sufficient to provide an aqueous suspension of cells in a concentration sufficient to genetically transform the dicotyledonous plant to enhance root growth; and
   (b) *A. radiobacter* in an amount sufficient to diminish the *A. rhizogenes* to substantially noninfective levels.

3. A composition as claimed in claim 2 in which the *A. rhizogenes* and the *A. radiobacter* are contained as separate units, with at least one being present in peat.

4. A composition for the genetic transformation of dicotyledonous plants for the beneficial growth of roots which comprises:
   (a) root-inducing *A. rhizogenes* in a concentration sufficient to provide an aqueous suspension of cells thereof in a concentration of at least about 1.07 cells/ml; and
   (b) *A. radiobacter* in an amount to provide an effective concentration in cells per milliliter such that cell ratio of *A. rhizogenes* to *A. radiobacter* is at least about 4 to 1.

5. A composition as claimed in claim 4 in which the *A. rhizogenes* and the *A. radiobacter* are contained as separate units, with at least one being present in peat.

6. A composition as claimed in claim 4 in which the cell ratio of *A. rhizogenes* to *A. radiobacter* is from about 4 to 1 to about 8 to 1.

7. A composition as claimed in claim 5 in which the cell ratio of *A. rhizogenes* to *A. radiobacter* is from about 4 to 1 to about 8 to 1.

8. A composition as claimed in claim 4 in which the *A. rhizogenes* comprises *A. rhizogenes* TR 105 and in which the *A. radiobacter* comprises *A. radiobacter* K 84.

9. A composition as claimed in claim 4 in which the *A. rhizogenes* comprises *A. rhizogenes* ATCC 39207.

10. A composition as claimed in claim 4 in which the *A. radiobacter* comprises *A. radiobacter* K 84.

11. A composition as claimed in claim 9 in which the *A. radiobacter* comprises *A. radiobacter* K 84.

12. A process for genetically transforming dicotyledonous plants which comprises contacting roots of the dicotyledonous plant having exposed pericycle to the transforming action of root-inducing *A rhizogenes* for a time sufficient to transform the dicotyledonous plant for enhanced root growth, and contacting the plant with *A. radiobacter* for a time sufficient to diminish the *A. rhizogenes* to substantially noninfective levels.

13. A process as claimed in claim 12 in which the *A. rhizogenes* comprises *A. rhizogenes* TR 105.

14. A process as claimed in claim 12 in which the *A. rhizogenes* comprises *A. rhizogenes* ATCC 39207.

15. A process as claimed in claim 11 in which the *A. radiobacter* comprises *A. radiobacter* K-84.

16. A process for genetically transforming dicotyledonous plants which comprises contacting roots of the dicotyledonous plant having exposed pericycle to the action of *A. rhizogenes* in a medium in which root-inducing *A. rhizogenes* is present in a concentration equivalent of an aqueous suspension of at least $10^8$ cells/ml for at least about 20 hours and sufficient to genetically transform the dicotyledonous plant and enhance root growth, then contacting the plant with *A. radiobacter* present in a medium in which the concentration of *A. radiobacter* is present in a concentration equivalent a suspension of about $10^7$ cells/ml for a time sufficient to diminish *A. rhizogenes* to substantially noninfective levels.

17. A process as claimed in claim 16 in which contact with *A. rhizogenes* is for at least about 24 hours.

18. A process as claimed in claim 17 in which the *A. rhizogenes* comprises *A. rhizogenes* TR 105.

19. A process as claimed in claim 17 in which the *A. rhizogenes* comprises *A. rhizogenes* ATCC 39207.

20. A process as claimed in claim 17 in which the *A. radiobacter* comprises *A. radiobacter* K-84.

21. A process as claimed in claim 18 in which the *A. rhizogenes* comprises *A. rhizogenes* TR 105.

22. A process as claimed in claim 18 in which the *A. rhizogenes* comprises *A. rhizogenes* ATCC 39207.

23. A process for genetically transforming dicotyledonous plants which comprises exposing roots of a dicotyledonous plant having a pericycle receptive to *A. rhizogenes* to a mixture of root-inducing *A. rhizogenes* and *A. radiobacter* contained in a medium wherefrom the *A. rhizogenes* can transform the dicotyledonous plant upon exposure of at least about 20 hours, the *A. rhizogenes* being present in the medium in a quantity equivalent of a suspension concentration of at least $10^8$ cells/ml of water and in which the cell ratio of *A. rhizogenes* to *A. radiobacter* is at least 4 to 1.

24. A process as claimed in claim 23 in which transformation occurs in at least about 24 hours.

25. A process as claimed in claim 23 in which the medium is aqueous and the *A. rhizogenes* and the *A. radiobacter* are contained in an aqueous suspension and in which the cell ratio of *A. rhizogenes* to *A. radiobacter* is from about 4 to 1 to about 8 to 1.

26. A process as claimed in claim 23 in which the *A. rhizogenes* and the *A. radiobacter* are provided from peat.

27. A process as claimed in claim 25 in which the *A. rhizogenes* and the *A. radiobacter* are provided from peat.

28. A process as claimed in claim 23 in which the *A. rhizogenes* comprises *A. rhizogenes* ATCC 39207.

29. A process as claimed in claim 23 in which the *A. rhizogenes* comprises *A. rhizogenes* ATCC 39207.

30. A process as claimed in claim 25 in which the *A. rhizogenes* comprises *A. rhizogenes* ATCC 39207.

31. A process as claimed in claim 12 in which the *A. radiobacter* comprises *A. radiobacter* K-84.

32. A process as claimed in claim 24 in which the *A. radiobacter* comprises *A. radiobacter* K-84.

33. A process as claimed in claim 25 in which the *A. radiobacter* comprises *A. radiobacter* K-84.

34. A process as claimed in claim 26 in which the *A. radiobacter* comprises *A. radiobacter* K-84.

35. A process as claimed in claim 27 in which the *A. radiobacter* comprises *A. radiobacter* K-84.

36. A process for genetically transforming dicotyledonous plants which comprises exposing roots of a dicotyledonous plant having a pericycle receptive to *A. rhizogenes* to *A. rhizogenes* ATCC 39207 in a medium wherefrom the *A. rhizogenes* ATCC 39207 can transform the dicotyledonous plant upon exposure of at least about 20 hours.

37. A process as claimed in claim 36 in which the transformation occurs in at least about 24 hours.

38. A composition for the genetic transformation of dicotyledonous plants for the beneficial growth of roots which comprises:
(a) root-inducing *A. rhizogenes* selected from the group consisting of *A. rhizogene* TR 105 and ATCC 39207 in a concentration sufficient to provide an aqueous suspension of cells thereof in a concentration of at least about $10^7$ cells/ml; and
(b) *A. radiobacter* K-84 in an amount to provide an effective concentration in cells per milliliter such that cell ratio of *A. rhizogenes* to *A. radiobacter* is at least about 4 to 1 to about 8 to 1.

39. A process for genetically transforming dicotyledonous plants which comprises exposing roots of a dicotyledonous plant having a pericycle receptive to *A. rhizogenes* to a mixture of root-inducing *A. rhizogenes* selected from *A. rhizogenes* TR 105 and *A. rhizogenes* ATCC 39207 and *A. radiobacter* K-84 contained in a medium wherefrom the *A. rhizogenes* can transform the dicotyledonous plant upon exposure of at least about 20 hours, the *A. radiobater* K-84 being present in the medium in a quantity equivalent of a suspension concentration of at least $10^8$ cells/ml of water and in which the cell ratio of *A. rhizogenes* to *A. radiobacter* is at least 4 to 1 to about 8 to 1.

* * * * *

UNITED STATES PATENT AND TRADEMARK OFFICE
CERTIFICATE OF CORRECTION

PATENT NO. : 4,588,693
DATED : May 13, 1986
INVENTOR(S) : Gary A. Strobel

It is certified that error appears in the above-identified patent and that said Letters Patent is hereby corrected as shown below:

Column 1, line 28, "A. rhizogeneshas" should read -- $\underline{A.\ rhizogenes}$ has --.

Column 4, line 20, "x" should read --$\bar{x}$--.

Column 5, line 16, "4.2" should be -- 4.5 --;
Column 5, line 26, "to a to a cell" should read -- to a cell --.

Column 7, line 41, claim 4, "1.07" should be -- $10^7$ --.

Signed and Sealed this

Twenty-third Day of December, 1986

*Attest:*

DONALD J. QUIGG

*Attesting Officer*   *Commissioner of Patents and Trademarks*